United States Patent [19]

Reul et al.

[11] Patent Number: 5,081,150
[45] Date of Patent: Jan. 14, 1992

[54] CALCIUM LACTATE-GLYCEROL ADDUCT, A PROCESS FOR ITS PREPARATION

[75] Inventors: Bernhard Reul, Königstein; Walter Petri, Niedernhausen, both of Fed. Rep. of Germany

[73] Assignee: Hoechst Aktiengesellschaft, Frankfurt am Main, Fed. Rep. of Germany

[21] Appl. No.: 512,078

[22] Filed: Apr. 12, 1990

[30] Foreign Application Priority Data

Mar. 27, 1987 [DE] Fed. Rep. of Germany ....... 3710177

[51] Int. Cl.⁵ .............................................. A61K 31/19
[52] U.S. Cl. .................................... 514/557; 426/648; 562/589
[58] Field of Search ........................ 562/589; 514/557; 426/648

[56] References Cited

U.S. PATENT DOCUMENTS

| 2,420,255 | 5/1947 | Lock | 562/589 |
| 4,013,773 | 3/1977 | Murakaoni et al. | 574/784 |

FOREIGN PATENT DOCUMENTS

| 485664 | 8/1952 | Canada | 562/589 |
| 331695 | 4/1920 | Fed. Rep. of Germany . | |
| 53-104720 | 9/1978 | Japan | 562/589 |

*Primary Examiner*—Bruce Gray
*Attorney, Agent, or Firm*—Finnegan, Henderson, Farabow, Garrett and Dunner

[57] ABSTRACT

Calcium lactate-glycerol adduct, a molecular compound of 1 mole of calcium lactate and 2 moles of glycerol, and a process for its preparation are described. The adduct can be used as a calcium donor or auxiliary in pharmacy, cosmetics and the production of foodstuffs.

7 Claims, No Drawings

CALCIUM LACTATE-GLYCEROL ADDUCT, A PROCESS FOR ITS PREPARATION

This is a continuation of application Ser. No. 07/173,466 filed Nov. 25, 1988 now abandoned.

DESCRIPTION

The invention relates to calcium lactate-glycerol adduct, which is a solid, pulverulent, crystalline reaction product between calcium lactate and glycerol, and a process for the preparation of this novel substance. The invention furthermore relates to the use of the adduct in pharmacy, cosmetics and foodstuffs.

Calcium lactate-glycerol adduct is a molecular compound between 1 mole of calcium lactate and 2 moles of glycerol, of the formula I

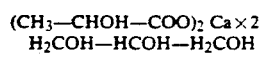

I

The process for its preparation comprises reacting calcium lactate with anhydrous glycerol in a molar ratio of 1 to at least 2, while warming in an anhydrous $C_1$- to $C_3$-alcohol, cooling the resulting clear solution and separating off the calcium lactate-glycerol adduct.

The calcium lactate is advantageously used either in the form of hydrates, for example the 5-hydrate, or in anhydrous form. In the reaction, at least 2 moles, preferably 4 moles, of glycerol are added to 1 mole of calcium lactate. The anhydrous glycerol is preferably mixed with anhydrous methanol, mixtures of 1 - 5 parts,* in particular 2 parts,* of methanol with 1 - 7, in particular 3 parts,* of glycerol preferably being used. The reaction mixture is heated to the boiling point under reflux; * by weight a clear solution is formed, from which the adduct precipitates in the form of granular crystals on cooling. For complete crystallization, the solubility of the adduct in the glycerol/methanol reaction mixture can be reduced by adding acetone (equal parts by weight of acetone, based on the glycerol employed). The substance is washed with a methanol/acetone mixture for complete removal of the glycerol. The adduct is separated off, for example, by filtration.

The product is white, solid, crystalline, finely powdered, free-flowing, pourable and physiologically tolerated.

It was surprising that, in spite of the high glycerol content (45.7% weight/weight), the novel substance is considerably less hygroscopic than anhydrous glycerol.

Another advantage is that the novel substance has a considerably higher short-term solubility than calcium lactate, as the following comparison shows:

Solubility in water at room temperature under constant conditions

| Solubility after (minutes) | Calcium lactate × 5 $H_2O$. MW = 308 | Calcium lactate-glycerol adduct MW = 402 |
|---|---|---|
| 5 minutes | 7.7% (w/w) = 1% of Ca | 17.0% (w/w) = 1.70% of Ca |
| 15 minutes | — | 17.0% (w/w) = 1.70% of Ca |
| 1440 minutes | 7.7% (w/w) = 1% of Ca | 9.8% (w/w) = 0.98% of Ca |

(w/w = weight %)

The low absorption of water vapor and the high solubility of calcium lactate-glycerol adduct, combined with the other properties mentioned, makes the novel substance suitable as an auxiliary in all cases where calcium is required with a good solubility and good processability, such as, for example, in pharmacy, cosmetics or production of foodstuffs.

The novel substance has a neutral taste, so that it can also be used for oral calcium therapy. All oral formulation forms are suitable for this. They are prepared by known processes, i.e. the pulverulent, crystalline calcium lactate-glycerol adduct is mixed with the customary auxiliaries for the particular formulation form, and the mixture is granulated, if appropriate, and then processed, for example to tablets, soluble or water-suspendible powders, granules, hard gelatin capsules and soft gelatin capsules.

The adduct can also be incorporated into foodstuffs and restorative agents as a calcium donor. The adduct per se or the adduct in granule form is suitable for this. The novel substance furthermore has a good dermal tolerability, so that it can also be used for dermal calcium therapy. The anhydrous dermal formulation forms, such as, for example, ointments and powders, are preferably suitable for this. For this use form, the pulverulent, crystalline calcium lactate-glycerol adduct is micronized and then incorporated into ointment and powder bases by known processes.

As well as having these possible uses in the field of foodstuffs and restorative agents and calcium therapy, calcium lactate-glycerol adduct can also be used as a tableting auxiliary, for example for promoting compacting, instead of lactose or as a filler, on the basis of its physical properties and technological peculiarities.

Because of its good physiological tolerability and as a result of its favorable dissolving properties, the novel substance finds a particular use in solid drug delivery systems (DDS), for example in moldings, extrudates, pellets or microcapsules, in that calcium lactate-glycerol adduct controls the release of the active substances incorporated.

The corresponding known processes are used to produce the drug delivery systems.

From the pharmaceutical technology point of view and from the point of view of calcium therapy, the novel calcium compound, calcium lactate-glycerol adduct, as a specific auxiliary for pharmacy and cosmetics, is a distinct advance over the prior art because of its particular physical properties coupled with a good physiological tolerability.

PREPARATION EXAMPLES

EXAMPLE 1

30.8 g of calcium lactate × 5 $H_2O$ are heated in a solution of 92.0 g of anhydrous glycerol and 76.2 ml of methanol (anhydrous) under reflux for 10 minutes. The clear solution is cooled rapidly (5 minutes) to room temperature and 115 ml of acetone are added. After the mixture has been stirred for 24 hours, the crystals formed are filtered off with suction and dried at room temperature in vacuo for 24 hours.

Yield: 37.6 g = 93% of theory

EXAMPLE 2

30.8 g of calcium lactate × 5 $H_2O$ are heated in a solution of 92.0 g of anhydrous glycerol and 76.2 ml of methanol (anhydrous) at 50° C. for 20 minutes, with stirring. The clear solution is cooled slowly (2 hours) to room temperature, with stirring, seeded and stirred at room temperature for a further 24 hours. The crystal sludge formed is pressed off (2.5 bar) and the filter cake is washed with 50 ml of an acetone/methanol mixture (3:1*) and then dried in vacuo at room temperature for 24 hours. * parts by weight Yield: 30.6 g = 76% of theory Analysis of the reaction product:

|  | Analytical result | Theoretical value |
|---|---|---|
| Calcium | 9.70% | 9.95% |
| Lactate | 43.70% | 44.28% |
| Glycerol | 43.70% | 45.70% |

What is claimed is:

1. Calcium lactate-glycerol adduct of the formula I $$(CH_3-CHOH-COO)_2 \; Ca \times 2$$
$$H_2COH-HCOH-H_2COH \qquad I$$

2. A process for the preparation of the calcium lactate-glycerol adduct as claimed in claim 1, which comprises reacting calcium lactate with anhydrous glycerol in a molar ratio of 1 to at least 2, while warming in an anhydrous $C_1$- to $C_3$-alcohol, cooling the resulting clear solution and separating off the calcium lactate-glycerol adduct.

3. The adduct of claim 1, wherein said calcium lactate-glycerol adduct is a solid pulverulent, crystalline reaction product.

4. The adduct of claim 1, wherein the adduct is anhydrous.

5. A composition for calcium therapy which comprises an effective amount of the adduct of claim 1 with a pharmaceutically acceptable carrier.

6. A foodstuff comprising an effective amount of the adduct of claim 1 as a calcium donor together with an acceptable carrier.

7. A pharmaceutical composition for controlling the release of an active substance comprising the active substance and an effective amount of the adduct of claim 1 for said controlling.

* * * * *

UNITED STATES PATENT AND TRADEMARK OFFICE
CERTIFICATE OF CORRECTION

PATENT NO. : 5,081,150
DATED : January 14, 1992
INVENTOR(S) : BERNHARD REUL ET AL.

It is certified that error appears in the above-identified patent and that said Letters Patent is hereby corrected as shown below:

On the title page, item (63) continuing data should read--
Mar. 25, 1988--.

Signed and Sealed this

Fifteenth Day of June, 1993

Attest:

MICHAEL K. KIRK

Attesting Officer

Acting Commissioner of Patents and Trademarks